(12) United States Patent
Vijayaraghavan et al.

(10) Patent No.: US 9,040,723 B2
(45) Date of Patent: May 26, 2015

(54) METHOD OF SYNTHESIZING A SUBSTANTIALLY MONODISPERSED MIXTURE OF OLIGOMERS

(75) Inventors: Reena Vijayaraghavan, Palakkad Kerala (IN); Srinivas Pullela Venkata, Bangalore Karnataka (IN); Chandrashekar Aswathanarayanappa, Bangalore Karnataka (IN)

(73) Assignee: BIOCON LIMITED (IN)

( * ) Notice: Subject to any disclaimer, the term of this patent is extended or adjusted under 35 U.S.C. 154(b) by 607 days.

(21) Appl. No.: 13/054,418

(22) PCT Filed: Aug. 28, 2008

(86) PCT No.: PCT/IN2008/000545
§ 371 (c)(1),
(2), (4) Date: Jan. 14, 2011

(87) PCT Pub. No.: WO2010/007626
PCT Pub. Date: Jan. 21, 2010

(65) Prior Publication Data
US 2011/0118480 A1 May 19, 2011

(30) Foreign Application Priority Data

Jul. 14, 2008 (IN) .......................... 01694/CHE/2008

(51) Int. Cl.
| | | |
|---|---|---|
| C07D 207/46 | (2006.01) | |
| C08G 65/332 | (2006.01) | |
| C08G 65/333 | (2006.01) | |

(52) U.S. Cl.
CPC .......... *C07D 207/46* (2013.01); *C08G 65/3322* (2013.01); *C08G 65/33337* (2013.01)

(58) Field of Classification Search
None
See application file for complete search history.

(56) References Cited

U.S. PATENT DOCUMENTS

| | | | |
|---|---|---|---|
| 4,980,482 A | 12/1990 | Frazier | |
| 6,828,297 B2 | 12/2004 | Ekwuribe et al. | |
| 6,835,802 B2 | 12/2004 | Ekwuribe et al. | |
| 6,913,903 B2 | 7/2005 | Soltero et al. | |
| 7,060,675 B2 | 6/2006 | Ekwuribe et al. | |
| 7,605,123 B2 * | 10/2009 | Radhakrishnan et al. | 514/1.1 |
| 2006/0018874 A1 | 1/2006 | Radhakrishnan et al. | |

FOREIGN PATENT DOCUMENTS

| | | |
|---|---|---|
| EP | 0115816 | 8/1984 |
| EP | 1614419 | 1/2006 |
| WO | WO 97/03106 A1 | 1/1997 |
| WO | WO 00/09073 | 2/2000 |
| WO | WO 03/049699 A2 | 6/2003 |
| WO | WO 2005025498 | 3/2005 |
| WO | WO 2006/014673 | 2/2006 |

OTHER PUBLICATIONS

Bellouard, F. et al. "A convenient synthetic route to polyether-tagged cyclam ligands and their nickel derivatives." Eur. J. Org. Chem., vol. 1999, 1999, pp. 3257-3261.
Furniss, B.S. et al. 1989 in *Vogel's Textbook of Practical Organic Chemistry* 5$^{th}$ ed. Longman Scientific & Technical pp. 691.
Greene, T. W. et al. 1991 in *Protective Groups in Organic Synthesis* 2$^{nd}$ Ed. Wiley-Interscience pp. 245-247.
Larock, R.C. 1989 in *Comprehensive Organic Transformations—A guide to Functional Group Preparations* VCH Publishers pp. 963-978.
Yam, C.M. et al. 2006 "Preparation, characterization, resistance to protein adsorption, and specific avidin-biotin binding of poly(amidoamine) dendrimers functionalized with oligo(ethylene glycol) on gold" *Journal of Colloid and Interface Science* 296:118-130.
Zalipsky, S. 1995 "Functionalized Poly(ethylene glycols) for Preparation of Biologically Relevant Conjugates" *Bioconjugate Chemistry* 6(2): 150-165.
Japanese Office Action, corresponding to Japanese Patent Application No. 2011-518060, issued on May 7, 2013.

* cited by examiner

*Primary Examiner* — Sun Jae Yoo
(74) *Attorney, Agent, or Firm* — Marianne Fuierer; Moore & Van Allen, PLLC

(57) ABSTRACT

The present invention relates to methods of synthesizing oligomeric compounds, and more particularly, to methods of synthesizing oligomer compounds comprising polyethylene glycol moieties. The present invention provides improved methods for synthesizing oligomers comprising polyethylene glycol moieties. Methods according to embodiments of the present invention may utilize reaction conditions that are milder, efficacious than those taught by conventional methods.

11 Claims, No Drawings

METHOD OF SYNTHESIZING A SUBSTANTIALLY MONODISPERSED MIXTURE OF OLIGOMERS

RELATED APPLICATIONS

This application is a U.S. National Phase of International Application No. PCT/IN2008/000545, filed Aug. 28, 2008, designating the U.S. and published in English on Jan. 21, 2010 as WO2010/007626A1, which claims the benefit of Indian Application No. 01694/CHE/2008, filed Jul. 14, 2008.

FIELD OF THE INVENTION

The present invention relates to methods of synthesizing oligomeric compounds, and more particularly, to methods of synthesizing oligomer compounds comprising polyethylene glycol moieties. The present invention provides improved methods for synthesizing oligomers comprising polyethylene glycol moieties. Methods according to embodiments of the present invention may utilize reaction conditions that are milder and efficacious than those taught by conventional methods.

BACKGROUND AND PRIOR ART OF THE INVENTION

One of the most important strategies for improving administration of polypeptides has been the conjugation of polypeptides to various moieties, such as polymeric moieties, to modify the physiochemical properties of polypeptide drugs to increase resistance to acidic and enzymatic degradation and to enhance penetration of such drugs across mucosal membranes. For example, Abuchowski and Davis have described various methods for derivatizating enzymes to provide water-soluble, non-immunogenic, in vivo stabilized products ("Soluble polymers—Enzyme adducts", Enzymes as Drugs, Eds. Holcenberg and Roberts, J. Wiley and Sons, New York, N.Y., (1981)). Abuchowski and Davis discuss various ways of conjugating enzymes with polymeric materials, such as dextrans, polyvinyl pyrrolidones, glycopeptides, polyethylene glycol and polyamino acids. The resulting conjugated polypeptides are reported to retain their biological activities and solubility in water for parenteral applications.

Furthermore, in U.S. Pat. No. 4,179,337, Davis et al. report that polypeptides can be coupled to polyethylene glycol or polypropylene glycol having a molecular weight of 500 to 20,000 daltons to provide a physiologically active non-immunogenic water soluble polypeptide composition. The polyethylene glycol or polypropylene glycol is reported to protect the polypeptide from loss of activity and the composition can be injected into the mammalian circulatory system with substantially no immunogenic response. However, these conjugates may not be suitable for oral administration.

Other researchers have shown that polyethylene glycol linked to a protein improves stability against denaturation and enzymatic digestion. (Boccu et al. Pharmacological Research Communication 14, 11-120 (1982)). However, these polymers do not contain components for enhancing membrane interaction. Thus, the resulting conjugates suffer from the same problems as noted above and are not suitable for oral administration.

For example, U.S. Pat. No. 5,681,811 to Ekwuribe et al., and related U.S. Pat. Nos. 5,438,040 and 5,359,030, describe stabilized, conjugated polypeptide complexes including a therapeutic agent coupled to an oligomer that includes lipophilic and hydrophilic moieties. A preferred subset of the polypeptide-oligomer conjugates described in the '811 patent includes a polymer having a linear polyalkylene glycol moiety and a linear alkyl moiety.

In the present invention the inventors discuss novel synthesis methods of manufacturing monomethyl ethers of PEG (also known as methyl-terminated PEG or mPEG). The instant invention relates to synthesis of oligomers compounds that are convenient due to lesser number of reaction steps included with desirable reaction conditions with easy purification methods. The compounds of the present invention addresses the discussed problems, further the resulting conjugates of the present invention are suitable for oral administration with enhanced in-vivo bioavailability and other advantageous attributes.

OBJECTIVES OF THE PRESENT INVENTION

The principal object of the present invention is to provide an improved method for synthesizing oligomeric compounds.

Another object of the present invention is to provide an improved method for synthesizing oligomers comprising polyethylene glycol moieties.

STATEMENT OF THE INVENTION

Accordingly, the present invention provides a method of synthesizing a substantially monodispersed mixture of oligomers comprising polyethylene glycol moieties of compounds represented by Formula IV, said method comprising steps of:
a. Reacting a substantially monodispersed mixture of compounds having the structure of formula I

FORMULA I wherein $R^1$ is a lower or higher alkyl, n=1 to 20, and $X^+$ is a positive ion with tert-butyl acrylate in the presence of a base under conditions sufficient to provide compound of Formula II

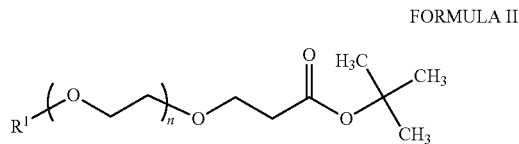

FORMULA II wherein $R^1$ is a lower or higher alkyl, n=1 to 20
b. Compound of Formula II is in turn converted to a compound of Formula III in the presence of p-toluene sulphonic acid (PTSA) and water.

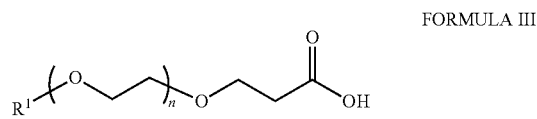

FORMULA III wherein $R^1$ is a lower or higher alkyl, n=1 to 20; and
c. Compound of Formula III is treated with thionyl chloride in an aprotic solvent and is activated in the presence of N-hydroxysuccinimide and tri-ethylamine to yield the compound of Formula IV

FORMULA IV

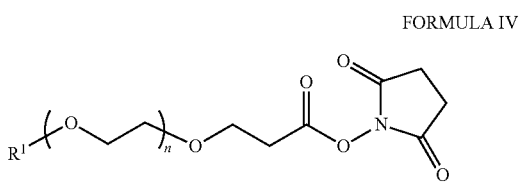

DETAILED DESCRIPTION OF THE INVENTION

The present invention is in relation a method of synthesizing a substantially monodispersed mixture of oligomers comprising polyethylene glycol moieties of compounds represented by Formula IV, said method comprising steps of:

a. Reacting a substantially monodispersed mixture of compounds having the structure of formula I

FORMULA I

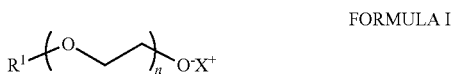

wherein $R^1$ is a lower or higher alkyl, n=1 to 20, and $X^+$ is a positive ion with tert-butyl acrylate in the presence of a base under conditions sufficient to provide compound of Formula II

FORMULA II

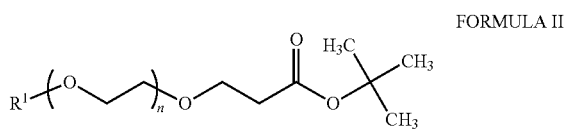

wherein $R^1$ is a lower or higher allyl, n=1 to 20 b. Compound of Formula II is in turn converted to a compound of Formula III in the presence of p-toluene sulphonic acid (PTSA) and water.

FORMULA III

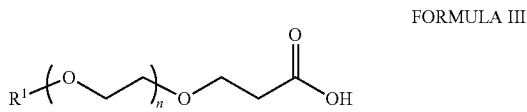

wherein $R^1$ is a lower or higher alkyl, n=1 to 20; and c. Compound of Formula III is treated with thionyl chloride in an aprotic solvent and is activated in the presence of N-hydroxysuccinimide and tri-ethylamine to yield the compound of Formula IV

FORMULA IV

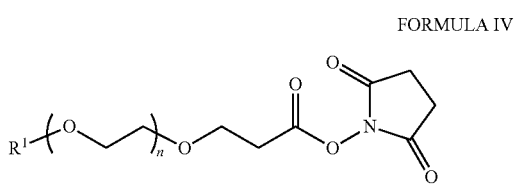

In another embodiment of the present invention the step (a) is performed at a temperature of 0° C. to 40° C.

Another embodiment of the present invention the step (a) is performed at a temperature of about 25° C.

In yet another embodiment of the present invention the base employed in step (a) is selected from the group comprising Sodium methoxide, Sodium ethoxide (NaOEt), Sodium metal (Na metal), Sodium hydroxide (NaOH), Potassium hydroxide (KOH), Lithium hydroxide (LiOH), Sodium hydride (NaH), Calcium hydroxide (Ca(OH)$_2$), Sodium carbonate (Na$_2$CO$_3$) and Barium hydroxide (Ba(OH)$_2$).

In still another embodiment of the present invention the base employed in step (a) is sodium methoxide.

In still another embodiment of the present invention the conversion of a compound of formula II to a compound of formula III in step (b) is carried out in the presence of compounds selected from the group comprising p-Toluene sulphonic acid (PTSA), Pyridinium p-toluenesulfonate (PPTS), Trifluoro acetic acid (TFA), Methane sulphonic acid (MeSO$_3$H), Ethane sulphonic acid (EtSO$_3$H), Benzene sulphonic acid (PhSO$_3$H), Sulphuric acid (H$_2$SO$_4$).

In still another embodiment of the present invention the step (b) is performed at a temperature of 0° C. to 80° C.

In still another embodiment of the present invention the step (b) is performed at a temperature of about 80° C.

In still another embodiment of the present invention the conversion of a compound of formula III to a compound of formula IV in step (c) is carried out in the presence of Thionyl chloride or Oxalyl chloride.

In still another embodiment of the present invention the conversion of a compound of formula III to a compound of formula IV in step (c) is carried out in the presence of an aprotic solvent.

In still another embodiment of the present invention the aprotic solvent employed in step (c) is selected from the group comprising N,N-dimethylacetamide (DMA), N,N-dimethylformamide (DMF), dimethyl sulfoxide, hexamethylphosphoric triamide, tetrahydrofuran (THF), dioxane, diethyl ether, methyl t-butyl ether (MTBE), toluene, benzene, hexane, pentane, N-methylpyrollidinone, dichloromethane, chloroform, tetrahydronaphthalene, decahydronaphthalene, 1,2-dichlorobenzene, 1,3-dimethyl-2-imidazolidinone, or a mixture thereof.

In still another embodiment of the present invention the aprotic solvent is N,N-dimethylformamide.

In still another embodiment of the present invention the step (c) is performed at a temperature of 0° C. to 40° C.

In still another embodiment of the present invention the compound of formula III is activated in the presence of N-hydroxysuccinimide In still another embodiment of the present invention the activation as in step (c) is carried out in the presence of an aliphatic amine selected from the group comprising monomethylamine, dimethylamine, trimethylamine, monoethylamine, diethylamine, triethylamine, monoisopropylamine, diisopropylamine, mono-n-butylamine, di-n-butylamine, tri-n-butylamine, monocyclohexylamine, dicyclohexylamine, or mixtures thereof.

In still another embodiment of the present invention the aliphatic amine is triethyl amine.

Embodiments of the present invention provide improved methods for synthesizing oligomers comprising polyethylene glycol moieties. Methods according to embodiments of the present invention utilize effective reaction conditions than that of the known conventional methods. For example, many, if not all, of the steps of methods according to embodiments of the present invention can be carried out employing desirable reaction conditions considerable reducing the reaction time. Additionally, methods according to embodiments of the present invention may be more efficient than the conventional methods. For example, methods according to embodiments of the present invention require fewer steps and/or less time than the conventional methods and employs novel intermediates as well. Methods according to embodiments of the present invention provide the ability to manufacture oligomers comprising polyethylene glycol moieties.

The invention will now be described with respect to preferred embodiments described herein. It should be appreciated however that these embodiments are for the purpose of illustrating the invention, and are not to be construed as limiting the scope of the invention as defined by the claims.

As used herein, the term "substantially monodispersed" is used to describe a mixture of compounds wherein at least about 95 percent of the compounds in the mixture have the same molecular weight.

As used herein, the term "monodispersed" is used to describe a mixture of compounds wherein about 100 percent of the compounds in the mixture have the same molecular weight.

As used herein, the term "PEG" refers to straight or branched polyethylene glycol polymers, and includes the monomethylether of polyethylene glycol (mPEG). The terms "PEG subunit" and polyethylene glycol subunit refer to a single polyethylene glycol unit, i.e., —(CH2CH2O)—.

As used herein, the term "lower alkyl" refers to substituted or unsubstituted alkyl moieties having from 1 to 5 carbon atoms.

As used herein, the term "higher alkyl" refers to substituted or unsubstituted alkyl moieties having 6 or more carbon atoms.

According to certain embodiments of the instant invention a method of synthesizing substantially monodispersed mixtures of oligomers comprising polyethylene glycol moieties comprises:

Reacting a substantially monodispersed mixture of compounds having the structure of formula I

FORMULA I

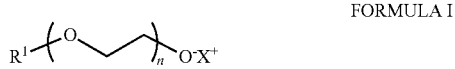

wherein $R^1$ is a lower or higher alkyl, n=1 to 20, and $X^+$ is a positive ion.

with tert-butyl acrylate in the presence of a base under conditions sufficient to provide compound of Formula II

FORMULA II

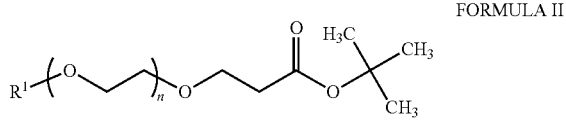

wherein $R^1$ is a lower or higher alkyl, n=1 to 20

Compound of Formula II is in turn converted to a compound of Formula III in the presence of p-Toluene sulphonic acid (PTSA) and water.

FORMULA III

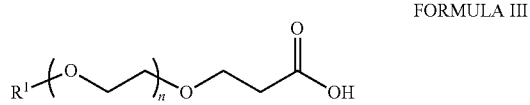

wherein $R^1$ is a lower or higher alkyl, n=1 to 20 and compound of Formula III is treated with thionyl chloride in an aprotic solvent is and activated in the presence of N-hydroxysuccinimide and tri-ethylamine to yield the compound of Formula IV

FORMULA IV

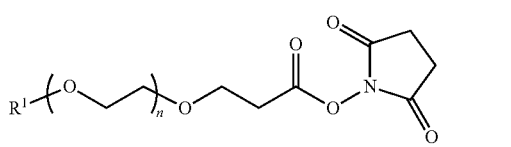

According to specific aspects of the present invention, a substantially monodispersed mixture of oligomers is as illustrated in Scheme I:

SCHEME I

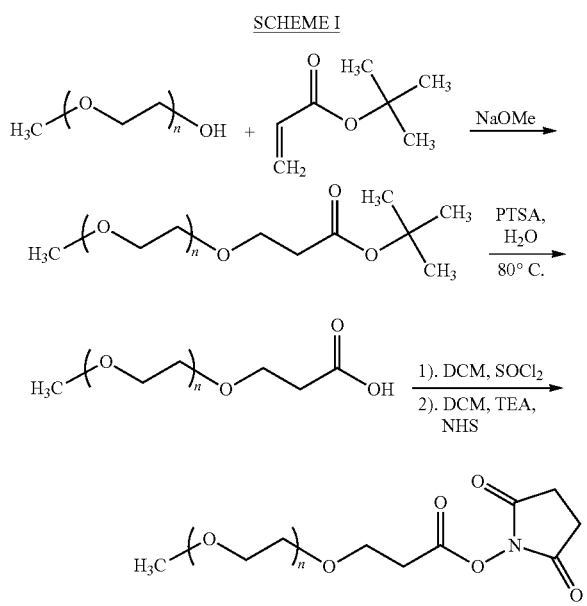

n = 1 to 20

Reaction 1 to obtain the compound of Formula II is preferably performed between about 0° C. and about 40° C., is more preferably performed between about 15° C. and about 35° C. and is most preferably performed at room temperature approximately about 25° C. Reaction 1 may be performed for various periods of time as will be understood by those skilled in the art. Reaction 1 is preferably performed for a period of time between about 0.25, 0.5 or 0.75 hours and about 2, 4, 8 to 10 hours.

Reaction 1 may be performed in the presence of a base such as Sodium methoxide, but not limited to Sodium ethoxide (NaOEt), Sodium metal (Na metal), Sodium hydroxide (NaOH), Potassium hydroxide (KOH), Lithium hydroxide (LiOH), Sodium hydride (NaH), Calcium hydroxide (Ca (OH)$_2$), Sodium carbonate (Na$_2$CO$_3$), Barium hydroxide (Ba (OH)$_2$) and the like.

Reaction 2 to convert compound of Formula II to compound of Formula III may be carried out in the presence of p-Toluene sulphonic acid (PTSA), Pyridinium p-toluenesulfonate (PPTS), Trifluoro acetic acid (TFA), Methane sulphonic acid (MeSO$_3$H), Ethane sulphonic acid (EtSO$_3$H), Benzene sulphonic acid (PhSO$_3$H), Sulphuric acid (H$_2$SO$_4$).

Reaction 2 may be performed for various periods of time as will be understood by those skilled in the art. Reaction 2 is preferably performed for a period of time between about 0.25, 0.5 or 0.75 hours and about 2, 4, 8 to 10 hours.

Reaction 2 to obtain the compound of Formula II is preferably performed between about 0° C. and about 40° C., is more preferably performed between about 15° C. and about 25° C.-35° C. and is most preferably performed at a temperature approximately about 80° C.

Reaction 3 to convert compound of Formula III to Formula IV is preferably performed between about 0° C. and about 40° C., is more preferably performed between about 15° C. and about 35° C. and is most preferably performed at room temperature approximately about 25° C.

Reaction 3 may be performed for various periods of time as will be understood by those skilled in the art. Reaction 1 is preferably performed for a period of time between about 0.25, 0.5 or 0.75 hours and about 2, 4, 8 to 10 hours. Reaction 3 can be carried out in the presence of Thionyl chloride (SOCl2) or Oxalyl chloride ((COCl)2) but preferably Thionyl chloride (SOCl2).

Reaction 3 is preferably carried: out in an aprotic solvent such as, but not limited to, N,N-dimethylacetamide (DMA), N,N-dimethylformamide (DMF), dimethyl sulfoxide, hexamethylphosphoric triamide, tetrahydrofuran (THF), dioxane, diethyl ether, methyl t-butyl ether (MTBE), toluene, benzene, hexane, pentane, N-methylpyrollidinone, dichloromethane, chloroform, tetrahydronaphthalene, decahydronaphthalene, 1,2-dichlorobenzene, 1,3-dimethyl-2-imidazolidinone, or a mixture thereof. More preferably, the solvent is DMF, dichloromethane or toluene While the oligomer represented as Formula III is activated using N-hydroxysuccinimide, it is to be understood that various other reagents may be used to activate oligomers of the present invention.

The activation is preferably carried out in the presence of an aliphatic amine including, but not limited to, monomethylamine, dimethylamine, trimethylamine, monoethylamine, diethylamine, triethylamine, monoisopropylamine, diisopropylamine, mono-n-butylamine, di-n-butylamine, tri-n-butylamine, monocyclohexylamine, dicyclohexylamine, or mixtures thereof. More preferably, the aliphatic amine is a tertiary amine such as triethylamine.

While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The description of a preferred embodiment and best mode of the invention known to the applicant at the time of filing the application has been presented and is intended for the purposes of illustration and description only. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

The technology of the instant application is further elaborated with the help of following examples. However, the examples should not be construed to limit the scope of the invention.

EXAMPLE 1

Preparation of tert-butyl-2,5,8,11-tetraoxatetradecan-14-oate

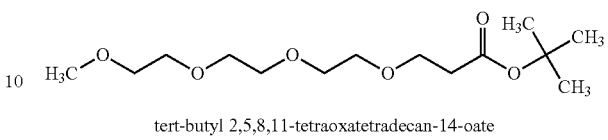

tert-butyl 2,5,8,11-tetraoxatetradecan-14-oate

Triethyleneglycol monomethyl ether (50 g, 304.5 mmol) was taken in tert-butyl acrylate (35.1 g, 274 mmol) and the mixture was stirred for 10 minutes. Sodium methoxide (1.97 g, 36.5 mmol) was added and stirred at ambient temperature for 8-10 hours. The reaction completion was checked by thin layer chromatography (TLC). The reaction mixture was diluted with ethyl acetate (200 mL) and the organic layer was washed with water, saturated brine solution and dried over sodium sulphate. The solvent was evaporated under reduced pressure to obtain tert-butyl 2,5,8,11-tetraoxatetradecan-14-oate (67 g, 75.3%).

EXAMPLE 2

Preparation of 2,5,8,11-tetraoxatetradecan-14-oic acid

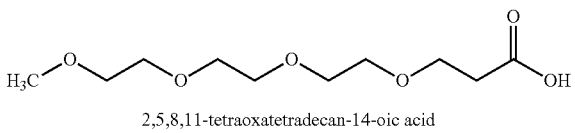 [SMILES: COCCOCCOCCOCCC(=O)O]

2,5,8,11-tetraoxatetradecan-14-oic acid

To tert-butyl 2,5,8,11-tetraoxatetradecan-14-oate (65 g, 222.6 mmol) (example-1), was added p-toluenesulfonic acid (21.16 g, 111 mmol) and water (31.7 mL). The contents were heated to 80° C. and stirred at that temperature for 2 h. The completion of the reaction was monitor by TLC. The reaction mixture was cooled to 0° C. and basified to pH 10 to 11 using sodium hydroxide solution (17.7 g dissolved in 65 mL water). The contents were stirred at 25-30° C. for 10 minutes. Added Ethyl acetate (65 mL×2), stirred and separated the layer. The aqueous layer was cooled to 0 to 5° C. and the pH was adjusted to 3.5 to 4 using 11 N HCl solution and the product was extracted to methylene chloride (120 ml×2). The combined organic layer was washed with water, brine solution and dried over sodium sulphate. The solvent was removed under vacuum to afford 2,5,8,11-tetraoxatetradecan-14-oic acid (40.5 g, 77.1%).

EXAMPLE 3

Preparation of 1-(4,7,10,13-tetraoxatetradecan-1-oyloxy)pyrrolidine-2,5-dione

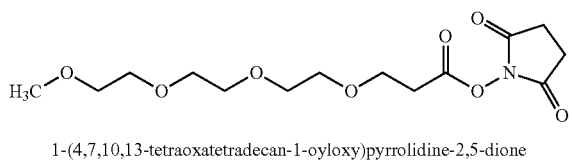 [SMILES: COCCOCCOCCOCCC(=O)ON1C(=O)CCC1=O]

1-(4,7,10,13-tetraoxatetradecan-1-oyloxy)pyrrolidine-2,5-dione 2,5,8,11-tetraoxatetradecan-14-oic acid (40 g, 169 mmol) (example 4) was dissolved in methylene chloride (200 mL), cooled to 0 to 5° C. and N,N'-dimethyl formamide (5 mL). Added slowly thionyl chloride (26.2 g, 220 mmol) was added by maintaining the temperature at 0 to 5° C. The reaction mixture was refluxed at 40 to 45° C. for 2 hours. The solvent was evaporated under vacuum and the syrup (acid chloride) obtained was dissolved in methylene chloride (40 mL). In a separate 500 ml 3-necked round bottom flask N-Hydroxy succinimide (13.6 g, 118 mmol) in methylene chloride (100 ml) was taken, the mass was cooled to 0 to 5° C. and triethylamine (22.2 g, 220 mmol) was added. Added slowly the acid chloride obtained above at 0 to 5° C. The temperature of the reaction mixture was brought to room temperature and stirred for 3 hours. The reaction completion was monitored by TLC (Thin layer chromatography). The mass was acidified to pH 4-5 and product was extracted to methylene chloride (100 ml×3). Combined organic layer was washed with 1.5 M HCl solution, water, followed by 10% sodium bicarbonate solution and saturated sodium chloride solution. The organic layer was dried over sodium sulphate and treated with neutral alumina (10% w.r.t [with respect to] starting material) and charcoal (10% w.r.t starting material) and filtered over celite. The filtrate was concentrated under vacuum to remove the solvent completely to obtain 1-(4,7,10,13-tetraoxatetradecan-1-oyloxy)pyrrolidine-2,5-dione (40 g, 71%).

The above description and examples have been given for ease of understanding only. No unnecessary limitations should be understood therefrom, as modifications will be obvious to those skilled in the art who will recognize that the invention can be practiced with modifications and variations within the spirit of the appended claims.

The technicalities reported herein overcome the problems of prior art and advance the art by providing a reaction method that inhibits loss of product and has ease of operation relative to other known methods. This system reduces costs by using described methodologies to achieve a given enhanced conversion efficiency relative to any known process, thus overcoming major disadvantages known in this domain of art.

We claim:

1. A method of synthesizing a substantially monodispersed mixture of oligomers comprising polyethylene glycol moieties of compounds represented by Formula IV, said method comprising steps of:
   (a) reacting a substantially monodispersed mixture of compounds having the structure of formula I FORMULA I
   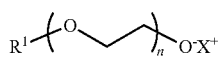

wherein $R^1$ is a lower or higher alkyl, n=1 to 20, and $X^+$ is a positive ion with tert-butyl acrylate in the presence of a base under conditions sufficient to provide compound of Formula II FORMULA II
   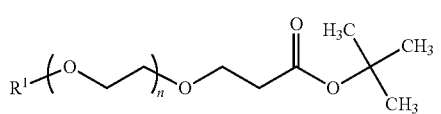

wherein $R^1$ is a lower or higher alkyl, n=1 to 20;

(b) converting the compound of Formula II to a compound of Formula III in the presence of acid and water, wherein the acid is selected from the group consisting of p-Toluene sulphonic acid (PTSA), Pyridinium p-toluenesulfonate (PPTS), Trifluoro acetic acid (TFA), Methane sulphonic acid ($MeSO_3H$), Ethane sulphonic acid ($EtSO_3H$), Benzene sulphonic acid ($PhSO_3H$) and Sulphuric acid ($H_2SO_4$)

FORMULA III
   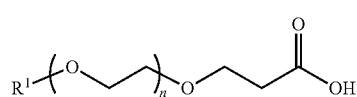

wherein $R^1$ is a lower or higher alkyl, n=1 to 20; and
   (c) dissolving the compound of Formula III in at least one aprotic solvent, adding thionyl chloride at a temperature from about 0 to 40° C. to form an acid chloride and activating the acid chloride in the presence of N-hydroxysuccinimide and an aliphatic amine selected from the group consisting of monomethylamine, dimethylamine, trimethylamine, monoethylamine, diethylamine, triethylamine, monoisopropylamine, diisopropylamine, mono-n-butylamine, di-n-butylamine, tri-n-butylamine, monocyclohexylamine, dicyclohexylamine and mixtures thereof, to yield the compound of Formula IV FORMULA IV
   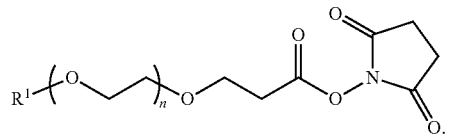

2. The method as claimed in claim 1, wherein the step (a) is performed at a temperature of 0° C. to 40° C.

3. The method as claimed in claim 2, wherein the step (a) is performed at a temperature of about 25° C.

4. The method as claimed in claim 1, wherein the base employed in step (a) is selected from the group consisting of Sodium methoxide, Sodium ethoxide (NaOEt), Sodium metal (Na metal), Sodium hydroxide (NaOH), Potassium hydroxide (KOH), Lithium hydroxide (LiOH), Sodium hydride (NaH), Calcium hydroxide ($Ca(OH)_2$), Sodium carbonate ($Na_2CO_3$) and Barium hydroxide ($Ba(OH)_2$).

5. The method as claimed in claim 4, wherein the base employed in step (a) is sodium methoxide.

6. The method as claimed in claim 1, wherein the step (b) is performed at a temperature of 0° C. to 80° C.

7. The method as claimed in claim 6, wherein the step (b) is performed at a temperature of about 80° C.

8. The method as claimed in claim 1, wherein the aprotic solvent employed in step (c) is selected from the group consisting of N,N-dimethylacetamide (DMA), N,N-dimethylformamide (DMF), dimethyl sulfoxide, hexamethylphosphoric triamide, tetrahydrofuran (THF), dioxane, diethyl ether, methyl t-butyl ether (MTBE), toluene, benzene, hexane, pentane, N-methylpyrollidinone, dichloromethane (DCM), chloroform, tetrahydronaphthalene, decahydronaphthalene, 1,2-dichlorobenzene, 1,3-dimethyl-2-imidazolidinone and a mixture thereof.

9. The method as claimed in claim 8, wherein the aprotic solvent is N,N-dimethylformamide.

10. The method as claimed in claim 1, wherein the step (c) further comprises combining the N-hydroxy succinimide in methylene chloride and cooling to a temperature of from about 0 to 5° C. and then adding the aliphatic amine.

11. The method as claimed in claim 1, wherein the aliphatic amine is triethyl amine.

* * * * *